United States Patent [19]

Dorin

[11] Patent Number: 5,248,769
[45] Date of Patent: Sep. 28, 1993

[54] PROCESS FOR RECOVERING REFRACTILE BODIES CONTAINING HETEROLOGOUS PROTEINS FROM MICROBIAL HOSTS

[75] Inventor: Glenn Dorin, San Rafael, Calif.

[73] Assignee: Cetus Oncology Corporation, Emeryville, Calif.

[21] Appl. No.: 798,837

[22] Filed: Nov. 25, 1991

Related U.S. Application Data

[63] Continuation of Ser. No. 200,741, May 31, 1988, abandoned, which is a continuation-in-part of Ser. No. 843,997, Mar. 25, 1986, Pat. No. 4,748,234, which is a continuation-in-part of Ser. No. 749,951, Jun. 26, 1985, abandoned.

[51] Int. Cl.$^5$ .......................... C07K 3/12; C07K 3/26
[52] U.S. Cl. .................................. 530/414; 435/69.1; 435/69.5; 435/69.51; 435/69.52; 530/351; 530/412; 530/427
[58] Field of Search ............. 530/351, 412, 416, 417, 530/422, 424, 427, 414; 435/69.1, 69.5, 69.51, 69.52

[56] References Cited

U.S. PATENT DOCUMENTS

| | | | |
|---|---|---|---|
| 4,426,323 | 1/1984 | Jain | 260/112 R |
| 4,450,103 | 5/1984 | Konrad et al. | 260/112 R |
| 4,462,940 | 7/1984 | Hanisch et al. | 260/112 R |
| 4,464,295 | 8/1984 | Bhaduri et al. | 260/112 R |
| 4,511,502 | 4/1985 | Builder et al. | 200/112 R |
| 4,511,503 | 4/1985 | Olson et al. | 260/112 R |
| 4,512,922 | 4/1985 | Jones et al. | 260/112 R |
| 4,518,526 | 5/1985 | Olson | 260/112 R |
| 4,530,787 | 7/1985 | Shaked et al. | 260/112 R |
| 4,569,790 | 2/1986 | Koths et al. | 260/112 R |
| 4,748,234 | 5/1988 | Dorin et al. | 530/412 |
| 4,929,700 | 5/1990 | Halenbeck et al. | 530/412 |
| 4,931,543 | 6/1990 | Halenbeck et al. | 530/412 |
| 4,935,369 | 6/1990 | Hayenga et al. | 530/412 |
| 5,162,507 | 11/1992 | Wolfe et al. | 530/416 |
| 5,183,746 | 2/1993 | Shaked et al. | 530/351 |

FOREIGN PATENT DOCUMENTS 0114506 8/1984 European Pat. Off.

OTHER PUBLICATIONS

Schnaitman, 1970, J. of Bact., 104:882-889.
Schnaitman, 1971, J. of Bact., 108:545-552.
Schnaitman, 1970, J. of Bact., 104:1404-1408.
Schnaitman, 1971, J. of Bact., 108:553-563.
Schnaitman, 1970, J. of Bact., 104:890-901.
Robinson et al., Proc. 4th Eur. Congress on Biotech., 1987, vol. 2, p. 627.
Kleid et al., 1984, Developments in Industrial Microbiol., 25:317-325.
Martson et al., 1984, Bio. Technol. pp. 800-804.
Hill et al., Infection Immunity, vol. 10(3) pp. 605-615, (1974).

*Primary Examiner*—Jeffrey E. Russel
*Attorney, Agent, or Firm*—Philip L. McGarrigle; Ling-Fong Chung; Jane McLaughlin

[57] ABSTRACT

A refractile material containing a heterologous protein is recovered from a host microorganism cell culture transformed to produce the protein. One recovery process involves first reducing the ionic strength of the culture medium prior to disruption to a level effective in preventing reaggregation of cellular debris with refractile material after disruption, disrupting the desalted culture, optionally adding material to the disruptate to create a density or viscosity gradient and separating the refractile material from the cellular debris by high-speed centrifugation. Preferably the salt removal step is carried out by diafiltration and the heterologous protein comprises recombinant M-CSF, IL-2 or IFN-$\beta$.

20 Claims, 5 Drawing Sheets

PROCESS FOR RECOVERING REFRACTILE BODIES CONTAINING HETEROLOGOUS PROTEINS FROM MICROBIAL HOSTS

This application is a continuation of application Ser. No. 07/200,741, filed May 31, 1988, now abandoned, which is a continuation-in-part application of Ser. No. 843,997, now U.S. Pat. No. 4,748,234, filed Mar. 25, 1986 and to be issued on May 31, 1988 which is a continuation-in-part of U.S. patent application Ser. No. 749,951 filed Jun. 26, 1985 and now abandoned.

FIELD OF THE INVENTION

This invention is in the general field of biochemical engineering. Specifically, this invention relates to a biochemical separation or recovery process in which refractile bodies containing microbially produced proteins are separated or recovered from the microorganism hosts which produce them.

BACKGROUND OF THE INVENTION

Recombinant DNA technology has enabled the expression of heterologous proteins in bacteria and other host cells at relatively high levels. Often, heterologous protein produced by the host cell precipitates inside the cell as opposed to being soluble in the cell. Methods to isolate these refractile bodies containing heterologous proteins offer substantial advantages to industrial scale purification schemes.

One such purification scheme is the invention disclosed in commonly owned U.S. Pat. No. 4,748,234, which is incorporated herein by reference in its entirety. It describes a process for recovering refractile bodies containing a heterologous protein from a host cell by first disrupting the cell wall and cell membrane of the microorganism. At least 99% of the salts are then removed from the disruptate and the desalted disruptate is redisrupted. Subsequently, the viscosity of the liquid is increased and the refractile bodies are separated from the cellular debris by high speed centrifugation. This process is effective, however, there is always a need for improvements which reduce time, labor or materials. Accordingly, it was discovered that if the first two steps are reversed, the third step can be eliminated. That is, if salt removal precedes cell disruption, the second disruption is unnecessary. Additionally, if the disruption is sufficient to result in a monolayer pellet rather than a bilayer pellet after centrifugation, the addition of a material to increase the density or viscosity of the disruptate is unnecessary. This invention, therefore, involves improvements in the methods disclosed in U.S. Pat. No. 4,748,234 whereby the number of processing steps is reduced, processing time is decreased, the process is easily scaled-up and maximum recovery of refractile material containing heterologous expression products is the ultimate result.

Becker et al., *Biotech. Advs.* (1983) 1:247-261 disclose the separation of refractile bodies from most of the cell debris and soluble impurities by a low-speed centrifugation. In addition, Kleid et al., ch. 25 in *Developments in Industrial Microbiology*, Vol. 25, p. 317-235 (*Society for Industrial Microbiology*, Arlington, Va. (1984) disclose purification of refractile bodies by homogenization followed by centrifugation. Also, Marston et al., *Bio/Technology* (September, 1984), pp. 800-804 describe release of inclusion bodies by enzymatic and mechanical disruption procedures as well as sonication. Purification and activity assurance of precipitated heterologous proteins is also described by U.S. Pat. Nos. 4,511,502; 4,511,503; 4,512,922; 4,518,526 and 4,620,948; and EP 114,506. These disclosures indicate that numerous steps involving repeated cell disruptions, resuspensions and centrifugations were required to obtain an isolated refractile body preparation. PCT application WO 85/05637 discloses a purification for gamma interferon which forms refractile bodies in *E. coli* involving cell disruption and subsequent centrifugation. U.S. Pat. No. 4,677,196, EP application 218,374 and EP application 212,960 describe the extraction, purification and activation of proteins produced as insoluble inclusion bodies. Insoluble material is obtained by disruption and centrifugation. U.S. Pat. No. 4,656,255 and EP application 215,625 discloses a process for increasing yields of recombinant proteins by recovering sidestream precipitates after initial solubilization and chromatography of inclusion bodies.

There remains a need in the art for a method of recovering refractile material containing heterologous expression products from the host cells which method is less costly, is easier to handle, faster and results in maximum recovery of pure protein in a biologically active form without use of chemical agents.

SUMMARY OF THE INVENTION

The present invention relates to a recombinant protein recovery process which can be easily scaled up and results in a pure, biologically active protein product. Specifically, the present invention relates to a process for recovering a refractile material containing a heterologous protein from a host microorganism cell in culture medium which cell is transformed to produce said protein, said process comprising:

(a) reducing the ionic strength of the culture medium to a level effective in preventing reaggregation of cellular debris with the refractile material after disruption;

(b) disrupting the microorganisms in said culture medium having reduced ionic strength;

(c) separating the refractile material from the cellular debris by high-speed centrifugation.

In preferred embodiments step (a) is accomplished by diafiltration, most preferably by cross-flow filtration. In yet another preferred embodiment, the desalted culture fluid produced by diafiltration is maintained at 4° C. for a time between 2 and 20 hours and diafiltration is repeated. In still another preferred embodiment greater than 99% by weight of the salts are removed from the culture medium. In yet still another preferred embodiment, diafiltration is accomplished with an exchange buffer volume ($V_x$) between five and fifteen times, preferably between five and ten times and most preferably between five and eight times, the culture fluid volume ($V_c$). In another preferred embodiment, a compound that increases the permeability of cell membranes may be added at some time before or during the diafiltration of step (a) to enhance the rate of salt removal. In another preferred embodiment, diafiltration is continued until there is no further decrease in the wet weight of the refractile material separated by centrifugation. In still another preferred embodiment, the refractile material has substantially the appearance of FIGS. 2C, 3C and 4C when examined under phase contrast microscopy.

In yet another preferred embodiment, the disruption of step (b) is adequate to produce a monolayer pellet the separation of step (c) without the addition of a mixture of sugars to increase the density or viscosity of the disruptate. In another preferred embodiment the separation of step (c) is accomplished in the presence of a sugar or a mixture of sugars.

The present invention also relates to a process that encompasses not only steps (a) through (c) as outlined above but also comprising an additional step of (d) adding a surfactant to the disruptate prior to centrifugation. In preferred embodiments step (d) is accomplished by the addition of nonidet P-40 or sodium deoxycholate.

DESCRIPTION OF THE PREFERRED EMBODIMENTS

Heterologous proteins are recovered in the form of refractile bodies by the present process. As used herein, the term "heterologous proteins" refers to proteins which are foreign to a host cell that is transformed to produce them. Thus, the host cell does not generally produce such proteins on its own. Such proteins are produced by recombinant DNA technology using techniques well known in the art. These proteins are often also hydrophobic, i.e., they are not soluble, or not readily soluble in aqueous medium under ambient conditions of room temperature and atmospheric pressure, at a neutral or physiological pH of between about 6.5 and 7.8.

The term "refractile material" designates material or bodies which refract light and appear as bright spots when viewed through a phase contrast microscope at magnifications as low as 1000 fold. Refractile material is also known as refractile or inclusion bodies. Examples of heterologous proteins which form refractile bodies in commonly found culture conditions include macrophage colony stimulating factor (M-CSF), interleukin-2 (IL-2), interferon-$\beta$ (IFN-$\beta$), envelope protein from feline leukemia virus antigen (FeLV), human growth hormone (hGH), bovine growth hormone (bGH), and certain proteins coated or fused with a virus such as FMD virus. Certain proteins, such as interferon-$\alpha$ (IFN-$\alpha$) and tumor necrosis factor (TNF), are more soluble in the cytoplasm.

Preferably the heterologous proteins recovered by the process described herein are M-CSF, IL-2 or IFN-$\beta$. As used herein, the term "M-CSF" refers to recombinant macrophage colony stimulating factor or macrophage colony stimulating factor-like polypeptides produced by a transformed microorganism whose amino acid sequence is the same as or similar or substantially homologous to the unglycosylated and/or glycosylated native macrophage colony stimulating factor. Substantially homologous means the sequences are identical or differ by one or more amino acid alterations (deletions, additions or substitutions) that do not cause an adverse functional dissimilarity between the synthetic and native protein. M-CSF is a protein which exhibits the spectrum of activity understood in the art for M-CSF—also known as CSF-1 i.e., when applied to the standard in vitro colony stimulating assay of Metcalf, D., *J. Cell. Physiol.* (1970) 76:89, it results in the formation of primarily macrophage colonies. Native M-CSF is a glycosylated dimer; in some instances dimerization is thought to be necessary for activity. Both the dimer and monomeric forms are within the envisioned embodiments of M-CSF. The monomeric form may be converted to the dimer by in vitro provision of suitable conditions, and the monomer is per se useful as an antigen to produce anti-M-CSF antibodies.

There appears to be some species specificity: Human M-CSF is operative both on human and on murine bone marrow cells; murine M-CSF does not show activity with human cells. Therefore, "human" M-CSF should be positive in the specific murine radioreceptor assay of Das, S. K. et al. *Blood* (1981) 58:630, although there is not necessarily a complete correlation. The biological activity of the protein will generally also be inhibited by neutralizing antiserum to human urinary M-CSF (Das, S. K., et al. supra). However, in certain special circumstances this criterion may not be met. For example, a particular antibody preparation may recognize a M-CSF epitope not essential for biological function, and which epitope is not present in the particular M-CSF mutein being tested. For purposes of definition herein, the M-CSF must stimulate the formation of monocyte/macrophage colonies using bone marrow cells from the appropriate species as starting materials, under most circumstances (see above) show inhibition of this activity by neutralizing antiserum against purified human urinary M-CSF, and, where appropriate for species type, exhibit a positive response to the radioreceptor assay.

The M-CSF proteins produced by the process disclosed herein may also be processed by proteolysis. It is believed that M-CSF may occur in nature in one or more C-terminally deleted forms. The primary amino acid structure (whether clipped at the C-terminus or not) may also aggregate to form complexes, most frequently dimers. Native human urinary M-CSF is isolated as a highly glycosylated dimer of 45-90 kd, depending on the method of measurement and identity of the reporter.

The recombinantly produced M-CSF reported by Wong, G. G., et al., (1987) *Science* 235:1504–1508, appears to have a subunit molecular weight of approximately 21 kd. On the other hand, the molecular weight calculated on the basis of the amino acid sequence deduced for the "short" 224 amino acid form of CSF (SCSF) by Kawasaki, E. S. et al., (1985) *Science* 230:291–296 and commonly owned copending U.S. Ser. No. 157,094 is on the order of 26 kd, while that of the "long" 522 amino acid form (LCSF) is calculated to be on the order of 55 kd, Wong G. G. et al., (supra) and Ladner, M. B. et al., (1987) *Embo J.* 6:2693–2698. When deleted constructs of these genes are expressed in *E. coli* (where glycosylation does not occur), they, of course, give rise to proteins of considerably lower molecular weight—e.g. 17-18 kd for SCSF/∇221.

It is, of course, well known that bacterially produced mature proteins which are immediately preceded by an ATG start codon may or may not include the N-terminal methionine in the form as produced and recovered. In addition, slight modification of the N-terminal sequence may aid in the processing of the N-terminal methionine, for example deletion of residues 1 and 2 (both glutamic acid) or residues 1-3 (glu-glu-val) aids in this manner. Accordingly, all of these forms may be produced by the process disclosed herein.

In summary, in addition to the N-terminal and C-terminal deletions and aggregations, individual amino acid residues in the chain may be modified by oxidation, reduction, or other derivatization, and these proteins may also be cleaved and/or aggregated to obtain fragments retain activity. Such alterations which do not destroy activity do not remove the protein sequence from the definition, and are specifically included. M-CSF derived from other species may fit the definition of a protein having activity of "human M-CSF by virtue of its display of the requisite pattern of activity as set forth above with regard to human substrate.

As used herein, the term "IL-2" refers to recombinant interleukin-2 or interleukin-2-like polypeptides produced by a transformed microorganism and whose amino acid sequence is the same as or similar or substantially homologous to the unglycosylated and/or glycosylated native interleukin-2. Examples of such IL-2s are those described in European published patent applications 91,539, 88,195, 109,748 and 200,280; those described in commonly owned U.S. Pat. No. 4,518,584; IL-2 described by Taniguchi et al., (1983) *Nature* 302:305-310 and Devos, R. et al., (1983) *Nucleic Acids Res.* 11:4307-4323; and bovine IL-2 as described by Cerretti et al., *Proc. Natl. Acad. Sci. USA* (1986) 83:3223-3227. The disclosures of all these references are incorporated herein by reference.

The IL-2s particularly preferred herein are those biologically active muteins (analogs) of human IL-2 in which amino acid residues not essential to biologically activity have been deliberately deleted or replaced with a conservative amino acid as indicated below. More specifically, preferred IL-2s include those wherein the cysteine residue at position 125 is replaced with another amino acid, preferably neutral or conservative, to eliminate sites for intermolecular crosslinking or incorrect intramolecular disulfide and, optionally, the N-terminal alanine residue of the native counterpart is eliminated. As used herein, such neutral or conservative amino acids are glycine, serine, valine, alanine, leucine, isoleucine, tyrosine and methionine. More particularly, preferred IL-2 muteins in the formulations of this invention are those wherein (1) the cysteine residue at amino acid position 125 of the native counterpart is replaced by a serine residue (designated IL-2$_{ser125}$) or alanine residue (designated IL-2$_{ala125}$); or (2) the initial alanine residue is eliminated and the cysteine at position 125 is replaced by serine (designated des-alanyl-IL-2$_{ser125}$).

Other IL-2s preferred herein are those biologically active muteins described in European Patent Publication 200,280 wherein oxidation-susceptible methionine residues are replaced with a neutral or conservative amino acid, a preferred mutein includes replacing the methionine at position 104 with a conservative amino acid such as alanine.

EP 200,280 also describes amino-terminal deletions of IL-2 wherein one or more of the first six amino acids are deleted. Other amino-terminal deletions of IL-2 are disclosed in *Chemical Abstracts* (1987) 106:(21);170236f, an abstract of Japanese Patent Publication No. 61/225199, published October 1986, wherein any one of the first 15 amino acids of IL-2 are deleted. PCT 87/04714, published Aug. 13, 1987 describes deletions or replacements of one or more of the amino acid residues in positions 2 to 11 and/or 128 to 133 from the amino-terminal alanine of IL-2.

As used herein the term "IFN-$\beta$" refers to recombinant interferon-beta or interferon-beta-like polypeptides produced by a transformed microorganism and whose amino acid sequence is the same as or substantially homologous to the unglycosylated and/or glycosylated native interferon-beta. The IFN-$\beta$s particularly preferred herein are those biologically active muteins of human IFN-$\beta$ in which amino acid residues not essential to biological activity have been deliberately deleted or replaced with a conservative amino acid as described for IL-2. More specifically, preferred IFN-$\beta$s include those wherein the cysteine residue at position 17 is replaced with another amino acid, preferably serine as disclosed in commonly owned U.S. Pat. No. 4,737,462 incorporated herein by reference in its entirety.

The precise chemical structure of the M-CSF, IL-2 or IFN-$\beta$ protein will depend on a number of factors. As ionizable amino and carboxyl groups are present in the molecule, a particular protein may be obtained as an acidic or basic salt, or in neutral form. All such preparations which retain their activity when placed in suitable environmental conditions are included in the definition of proteins herein. Further, the primary amino acid sequence of the protein may be augmented by derivatization using sugar moieties (glycosylation) or by other supplementary molecules such as lipids, phosphate, acetyl groups and the like, more commonly by conjugation with saccharides. Certain aspects of such agumentation are accomplished through post-translational processing systems of the producing host; other such modifications may be introduced in vitro. In any event, such modifications are included in the definition of protein herein so long as the activity of the protein, as defined above, is not destroyed. It is expected, of course, that such modifications may quantitatively or qualitatively affect the activity, either by enhancing or diminishing the activity of the protein in the various assays. Further, individual amino acid residues in the chain may be modified by oxidation, reduction or other derivatization, and the protein may be cleaved to obtain fragments which retain activity. Modification to the primary structure itself by deletion, addition or alteration of the amino acids incorporated into the sequence during translation can be made without destroying the activity of the protein. Such alterations which do not destroy activity do not remove the protein sequence from the definition.

As used herein the term "transformed" in describing host microorganism cell cultures denotes a microorganism that has been genetically engineered to produce a heterologous protein that possesses the activity of the native protein. Examples of transformed microorganisms are described in the examples of this application. Bacteria are preferred microorganisms for producing the protein. Synthetic protein may also be made by suitably transformed yeast and mammalian cells. *E. coli* is a particularly preferred host.

Cell growth conditions and cell concentration and disruption techniques are elaborated in commonly owned U.S. Pat. No. 4,798,234 as well as in the art. After the cells are harvested from the culture, they may be concentrated, for convenience, to about 20 to 150 mg/ml, preferably 80 to 100 mg/ml ($OD_{680}$40 to 300, preferably 160 to 200) by cross-flow filtration, centrifugation or other conventional methods.

Figure 1:
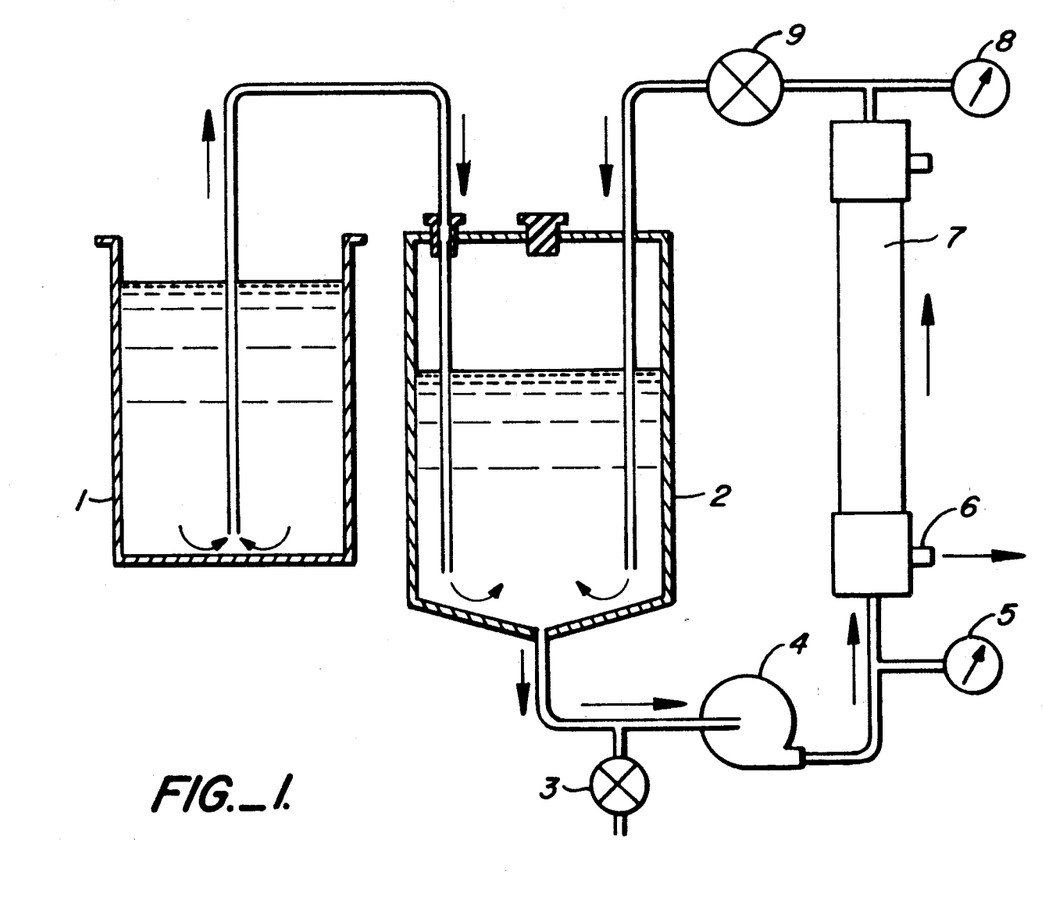
FIG. 1 is a diagram of the fluid flow arrangement of a diafiltration or cell washing system.

As used herein, "reducing the ionic strength of the cell culture medium so as to prevent reaggregation of cellular debris with the refractile material after disruption" refers to an active process by which salts are removed from the spent culture medium. "Ionic strength" refers to the conventional measure of ion concentration in aqueous solution. It is defined as one half of the sum (over all of the ions in solution) of the product of the concentration of each ion, times the square of the charge thereon. The preferred means of reducing the ionic strength is by diafiltration. "Diafiltration" or cell washing may be accomplished using hollow fiber or plate and frame cross-flow filtration systems. "Cross-flow filtration" refers to a mode of filtration in which a suspension of refractile material producing cells flows substantially parallel to a filter or membrane which is permeable to a component of the suspension other than the cells. The fluid flow arrangement and diafiltration procedure is diagramed in FIG. 1. A pump 4 draws cell culture fluid from a reservoir 2, then circulates it through the interiors of the filter element 7 and back to the reservoir 2. Transmembrane pressure monitored by gauges 5 and 8 causes solutes smaller than the molecular weight cut off (MWCO) of the membrane to be forced continuously through the membrane pores. This permeate is removed from porthole 6 and a simple method is used to maintain the culture fluid at a constant volume. The culture fluid reservoir 2 is sealed and a separate reservoir of exchange buffer 1 is prepared. Vacuum in the culture fluid reservoir 2 draws in solution from the exchange buffer reservoir 1 at a rate equal to the filtration rate. Back pressure valve 9 and drain valve 3 function to purge the system membrane pore size.

Membrane pore sizes appropriate for use in filter element 7 (FIG. 1) as described herein include any microporous or ultrafiltration membrane having a pore size ranging from about 100,000 MWCO-1.0 micron, preferably from 500,000 MWCO-1.0 micron and most preferably from 500,000 MWCO-0.2 micron. The selection of the appropriate membrane may be largely dictated by process economics.

Since solutes smaller than the membrane pore size are removed in the permeate, the degree of removal depends upon the "exchange buffer volume ($V_x$)" added relative to the "culture fluid volume (Vc)". The percent removal of these permeable solutes may be calculated according to the equation $1-e^{-V_x/V_c}$. If the cluture fluid volume ($V_c$) is replaced by an equal volume of exchange buffer ($V_x$), then $V_x/V_c=1$ and there is said to have been one volume change. When $V_x/V_c=5$, according to the above equation, 99.3% of the permeable solutes have been removed. As used herein, "permeable solutes", "ions" and "salts" are used interchangeably to denote charged species which contribute to the ionic strength.

Figure 2A:
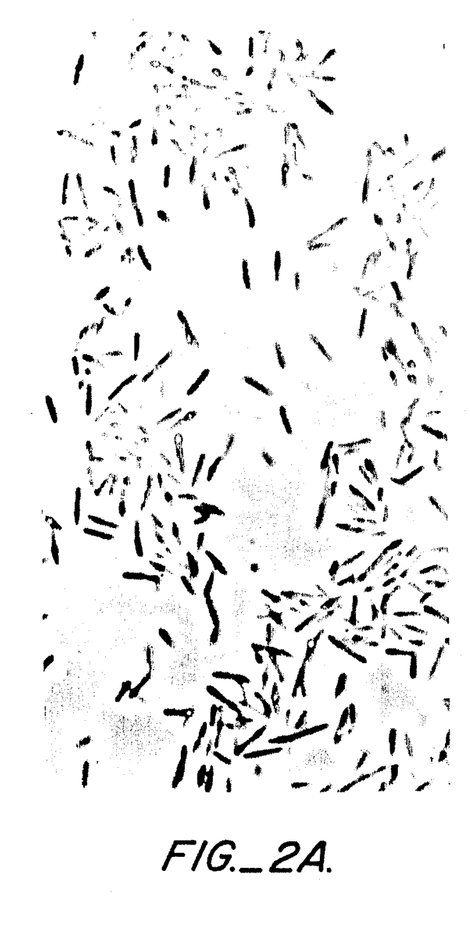
FIG. 2(A)-(C) shows photographs taken under a phase contrast microscope of cells containing refractile bodies comprising M-CSF before diafiltration and disruption (A), after disruption in the absence of diafiltration (B) and after diafiltration and disruption (C).
Figure 2B:
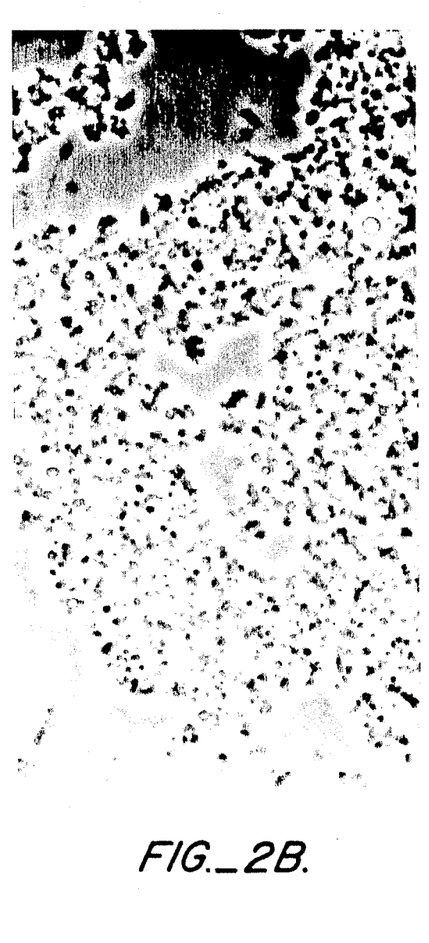
Figure 2C:
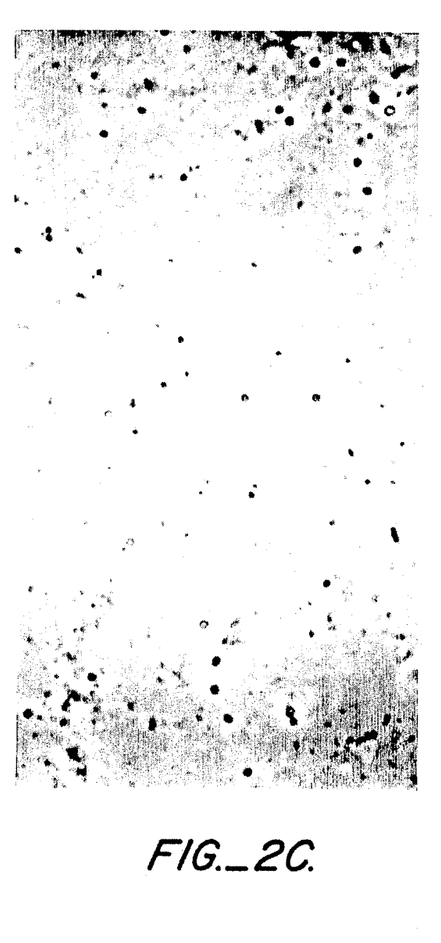
Figure 3A:
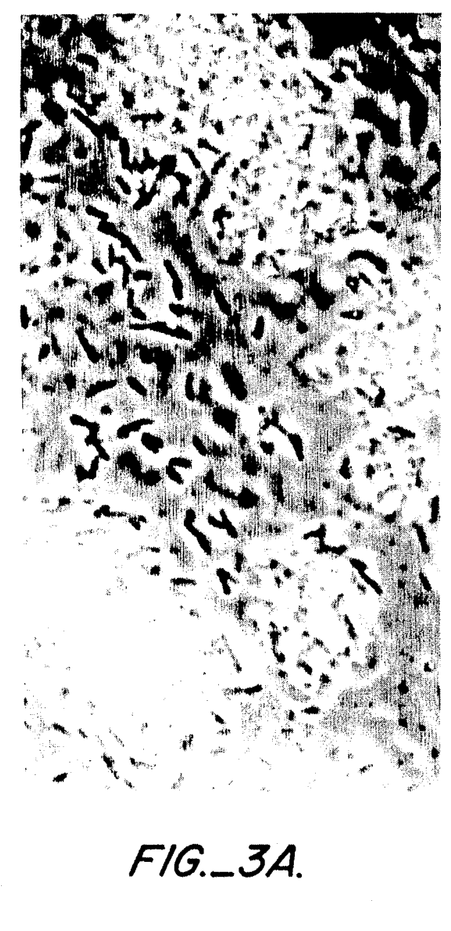
FIG. 3(A)-(C) shows photographs taken under a phase contrast microscope of cells containing refractile bodies comprising IL-2 before diafiltration and disruption (A), after disruption in the absence of diafiltration (B) and after diafiltration and disruption (C).
Figure 3B:
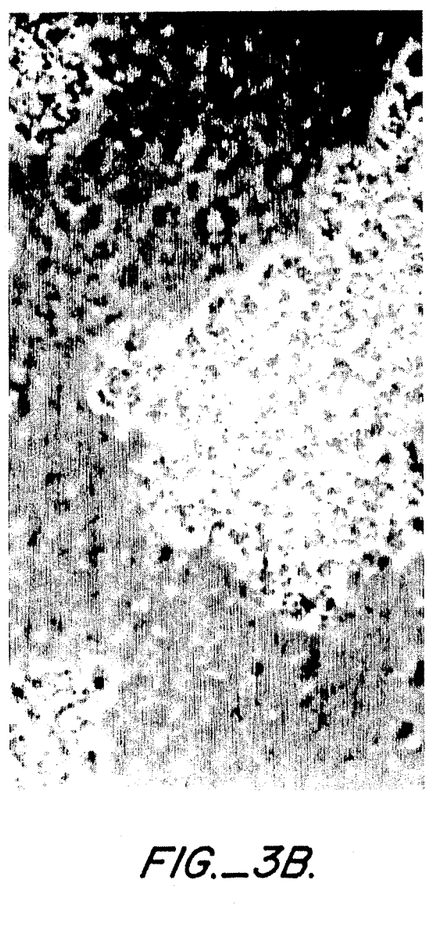
Figure 3C:
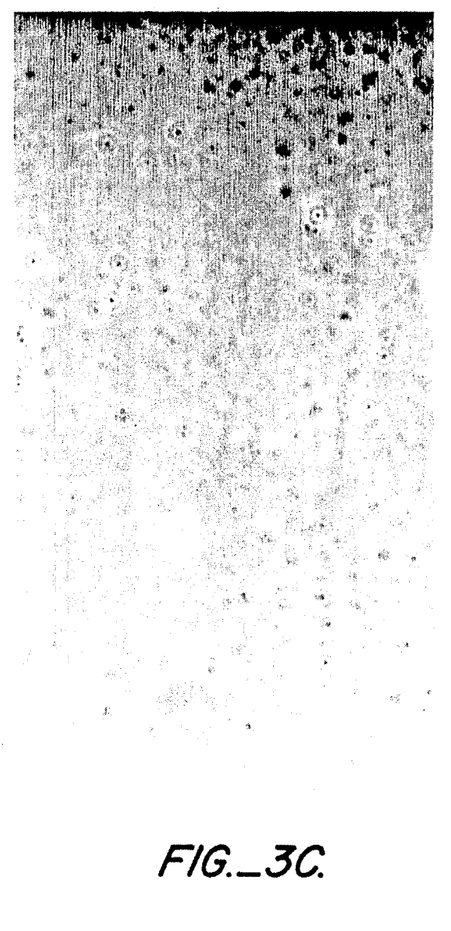
Figure 4A:
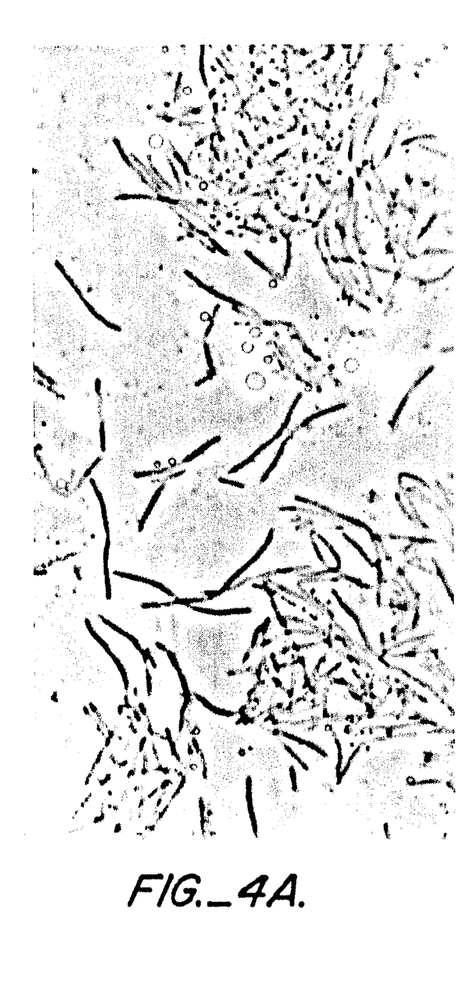
FIG. 4(A)-(C) shows photographs taken under a phase contrast microscope of cells containing refractile bodies comprising IFN-$\beta$ before diafiltration and disruption (A), after disruption in the absence of diafiltration (B) and after diafiltration and disruption (C).
Figure 4B:
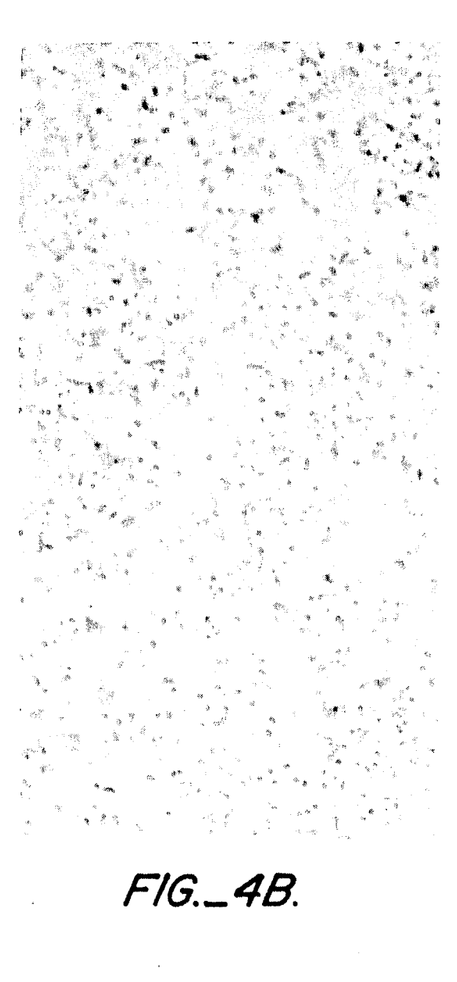
Figure 4C:
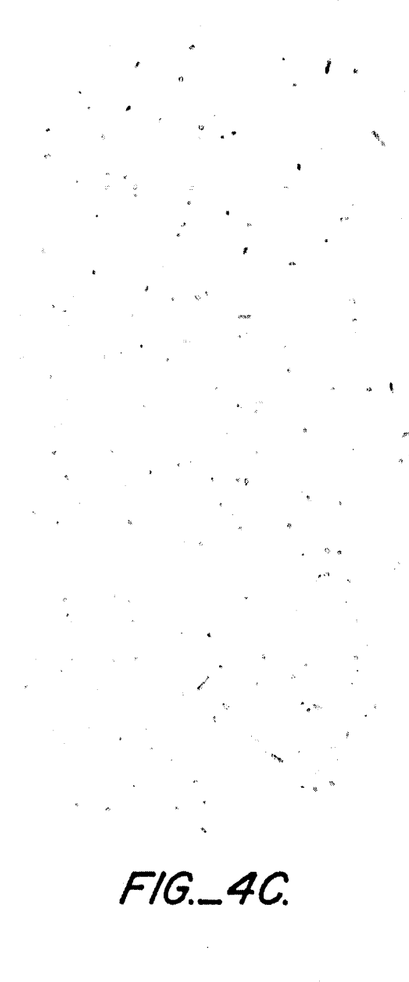

If diafiltration is employed to reduce the ionic strength of the cell culture medium, the preferred exchange buffer is 1-5 mM EDTA (pH8.5) most preferably 1-2 mM. In addition, Tris-HCl (pH8.0-8.5) may be added to the buffer at 5-15 mM. The length of time required for removal of sufficient salts from the culture medium by diafiltration may vary with the cultured recombinant microorganism and diafiltration conditions. The extent of diafiltration required can be monitored most preferably by visualization of a disrupted aliquot under the microscope to ensure minimal or no reaggregation of cellular debris with refractile material. After approximately 5 volume changes, it is generally appropriate to remove an aliquot from the culture fluid reservoir and disrupt the cells contained therein to determine whether the ionic strength has been reduced to a level sufficient to allow refractile material to be isolated free of cellular debris after disruption. FIGS. 2, 3 and 4 provide a comparison of cells producing three different recombinant proteins in the form of refractile material. Part A of each figure shows whole cells after harvest containing refractile material which as the term implies, refracts light and appears as bright spots when viewed through a phase contrast microscope. Part B of each figure shows the disrupted cells in the absence of any step to reduce the ionic strength. These part B photographs represent disrupted aliquots of the starting material for the diafiltration step. Part C of each figure shows the disrupted cells after the ionic strength has been reduced to a level sufficient to allow refractile material to be isolated free of cellular debris. These photographs represent disrupted aliquots of the diafiltration endpoint. In some cases, it may be preferable to diafilter the cell culture for a period of time or a certain $V_x/V_c$ value, hold the culture at 4° C. for an additional period of time between 2 and 20 hours to allow for the transfer of intracellular salts into the culture fluid and then resume diafiltration for a second time period.

There are at least two sources of the components that contribute to the ionic strength of the cell disruptate. One is the cell culture medium itself and the other is the intracellular ions which are released from the cell upon disruption. While the growth medium salts may be readily removed by diafiltration, the intracellular salts are transferred out of the cell into the extracellular culture fluid in a time-dependent fashion. It would be desirable to enhance the rate of this intracellular salt removal in order to minimize the time required for the effective reduction of the ionic strength of the culture fluid to a level which permits the separation of refractile material relatively free of cellular debris.

To accomplish this rate enhancement, the cell membrane permeability to ions may be increased. By "cell membrane permeability" is meant the characteristic of the inner cell or lipid bilayer membrane and of the outer cell wall to permit the transfer of compounds including solutes, salts or ions from one side to the other. This chemical permeabilization of the cells serves to enhance the rate at which intracellular salts are transferred into the culture fluid.

Compounds that increase the fluidity of the cell membrane and that result in increased cell membrane permeability without extensive breakage of the cell are known in the art. Such compounds may include detergents, anaesthetics known to act via membrane permeabilization, chaotropic agents and other membrane solubilizing agents. Preferred detergents include nonionic detergents, most preferably Triton X-100 ®. Preferred anaesthetics include chlorpromazine, ethanol, chlorfrom and ether. Preferred chaotropic agents include guanidine-HCl. Among other membrane solubilizing agents most preferred is dimethylsulfoxide (DMSO). Also preferred are combinations of these compounds, the preferred combination being Triton X-100 ® and guanidine-HCl. Appropriate concentrations for all chemical permeabilizers are in the prelytic range and will vary for the compound employed. Appropriate concentrations for Triton X-100 ® range from 0.1–3% (v/v), most preferably 1–2% (v/v). Preferred concentrations for guanidine-HCl range from 0.05–2M, most preferably 1–2M. In combination Triton X-100 ® is preferred in the range of 0.1–2% (v/v) and guanidine-HCl is preferred in the range of 0.05–2M. Most preferred is the combination of Triton X-100 ® at 2% (v/v) and guanidine-HCl at 0.05–0.5M.

As used herein the term "surfactant" refers to a substance having the ability to lower surface tension of an oil-water interface. A compound with this property comprises a molecule composed of hydrophobic and hydrophilic parts, so that it is concentrated at the interface, because these parts have affinities for different phases. Detergents are included among surfactants. Detergents may be either ionic or non-ionic depending on whether the hydrophilic portion of the molecule carries a charge or is uncharged. Preferred non-ionic detergents include nonidet P-40, Triton X-100 ®, the Tween ® series and the Brij ® series. Most preferred is the ethylene oxide polymer type known as nonidet P-40 or NP-40. Preferred ionic detergents include sodium deoxycholate (DOC), sodium caprylate, cetyltrimethyl ammonium bromide (CETAB) and taurodeoxycholate. Most preferred is sodium deoxycholate. The amount of surfactant required to reduce material having absorbance at 260 nm in the refractile body pellet depends upon the particular surfactant and the refractile body composition. For most surfactants, concentrations ranging from 0.1–5% are preferred, most preferred are concentrations ranging from 0.1–2%.

In the final step of the process to recover the refractile bodies, the refractile bodies containing the heterologous protein are separated from the cellular debris by high-speed centrifugation. By "high-speed centrifugation" is meant spinning the suspension in a centrifuge at about 10,000 to 40,000 times gravity, preferably about 10,000–20,000×g, for a suitable time period depending on the volume, generally about 10 minutes to seventy-two hours. If the density of the medium has been increased by the addition of a sugar or a mixture of sugars, the density will generally be too high to separate the particles by low-speed centrifugation. Therefore, if the centrifugation is carried out at low speeds (e.g., at 500 to 4,000×g), satisfactory results are not obtained. The exact centrifugation speed will depend on the protein and the final concentration of material added to create the gradient (e.g., sucrose). For example, interferon may require lower sucrose concentration to obtain maximal recovery, and thus the centrifugation speed may be lowered, or the centrifuge retention time decreased.

As used herein, "wet weight" refers to the mass of the refractile body pellet obtained after high speed centrifugation of the disruptate.

Sugars or mixtures of sugars which may be used to increase the density or viscosity of the disruptate as well as the conditions for centrifugation have been described in commonly owned U.S. Pat. No. 4,748,234. As mentioned earlier, the addition of a sugar or mixture of sugars to increase the density of the disruptate and allow the separation of less dense materials contaminating the refractile body preparation may be unnecessary if the disruption is extensive enough to render these materials so small as to be unsedimentable under the centrifugation conditions employed.

The following examples further illustrate the invention process. These examples are not intended to limit the invention in any manner.

EXAMPLE I

Purification of Refractile Bodies Containing Macrophage Colony Stimulating Factor (M-CSF)

*E. coli* strain DG116 transformed with plasmid vector pLCSF221A was deposited on Apr. 14, 1987 with the ATCC and given accession number 67390. The plasmid contains the gene encoding Asp59 LCSF/N v 3C v 221 which is disclosed in commonly owned copending patent applications U.S. Ser. Nos. 039,654 and 039,657, each incorporated herein by reference in its entirety. Cells were grown in a 100 L standard air-sparged Rushton turbine fermenter in basal medium containing 96 mM $(NH_4)_2SO_4$, 28 mM $KH_2PO_4$, 4 mM $Na_3$ citrate.2 $H_2O$, 1.7 ml/L TK9 (30 mM $ZnSO_4$, 30 mM $MgSO_4$, 1 mM $CuSO_4$), with sterile additions of 6.5 g/L glucose, 2.2 mM $MgSO_4.7$ $H_2O$, 95 $\mu$M $FeSO_4.7$ $H_2O$ and 26 mg/L thiamine-HCl at 30° C. until an $A_{680}$ of 10 was reached. The culture was then induced by temperature shift to 37° C. with concurrent sterile additions of casamino acids to about 2% (w/v) final concentration and $MgSO_4.7$ $H_2O$ to 1.7 mM final concentration.

Four hours post-induction, the cells were harvested by five-fold concentration and refractile bodies were visualized under a phase contrast microscope as shown in FIG. 2A. The concentrated culture was diafiltered against 10 volume changes of 5 mM EDTA (pH 8.5) using Dorr-Oliver tangential cross-flow microporous filtration. The cells were disrupted by three passes at 7,500 psi in a Manton-Gaulin high pressure mechanical cell homogenizer. Refractile bodies at this stage appeared relatively free of cellular debris after disruption as shown in FIG. 2C. This refractile body preparation is compared with the substantial aggregation of refractile bodies and cellular debris in FIG. 2B in which no diafiltration step for salt removal was carried out. 1-Octanol was added to 0.5% (v/v) and the homogenate was held overnight at 4° C.

The homogenate was made 25% sucrose by addition of a 63% w/v sucrose, 1 mM EDTA pH 8.0 solution. The insoluble protein fraction containing refractile material was separated from cell debris by continuous flow disc stack centrifugation (Westphalia SB7) at 9000×g, 1 L/minute and 4°–6° C. The wet pellet was mixed 50:50 (w/v) in deionized water and stored at −20° C. in 45 g aliquots.

EXAMPLE II

Purification of Refractile Bodies Containing Interleukin-2 (IL-2)

A. *E. coli* Expressing IL-2 Under the Control of the trp Promoter

*E. coli* K12/MM294-1 cells carrying pLW45 (ATCC No. 39626) as described in commonly owned U.S. Pat. No. 4,530,787 issued Jul. 23, 1985 were grown as described in commonly owned patent application U.S. Pat. No. 4,748,234. Refractile bodies were purified according to the following procedure. Eleven liters of cell culture was concentrated to 2 L using 1.0 micron microporous hydrophobic PTFE or polypropylene membranes at pH 8.5. The concentrated culture was diafiltered against 8 volume changes of 2 mM EDTA (pH8.5) using Dorr-Oliver tangential cross-flow microporous filtration. Diafiltration was carried out for about 1 hour followed by rinsing of the chamber with 2 mM EDTA (pH8.5). The final volume was 2.25L.

The diafiltered cell culture was disrupted by three passes at 7500 psi in a Manton-Gaulin high pressure mechanical cell homogenizer. The homogenate was made 25% sucrose by the addition of a 63% w/v sucrose solution. The refractile material was separated from cell debris by continuous centrifugation. The wet pellet was stored at −20° C.

B. *E.coli* Expressing IL-2 Under the Control of the $P_L$ Promoter.

*E.coli* strain MM294-1 transformed with plasmid vector pFC54.t was deposited pursuant to the Budapest Treaty in the CBS on Apr. 13, 1988, under accession number CBS 242.88. Plasmid pFC54.t has been disclosed in U.S. Pat. No. 4,666,848.

10L of cells were grown in medium containing 25 mM $KH_2PO_4$, 28 mM $(NH_4)_2SO_4$, 4.3 mM $Na_3$ citrate.$2H_2O$, 400 μM $FeCl_3.H_2O$, 40 μM $ZnCl_2$. $4H_2O$, 33.3 μM $CoCl_2.6H_2O$, 33.3 μM $NaMoO_4.2H_2O$, 26.6 μM $CaCl_2.2H_2O$, 29.3 μM $CuCl_2.2H_2O$, 32 μM $H_3BO_3$ and NaOH to pH 6.8. At an $A_{680}$ of 22, IL-2 synthesis was induced by raising the culture temperature from 30° to 37° C. Cells were harvested at three hours post-induction. Cells containing refractile bodies were visualized under a phase contrast microscope as shown in FIG. 3A.

The harvested cells from the fermentor, approximately 10 liters, were concentrated to about 3 liters and diafiltered against 15 volume changes (45 liters total) 5 mM Tris.HCL, 1 mM EDTA (pH 8.0). The membranes used were 0.2 micron PTFE membranes in a Ioplate ® configuration. Cell concentration and diafiltration took approximately 90–130 minutes at 25° C. Culture fluid reservoir samples were taken at 2, 4, 6, 8, 10 and 15 volume changes and after disruption, supernatants were analyzed for conductivity and absorbance at 280 and 260 nm while pellets were qualitatively evaluated for refractile body purity. The final diafiltered concentrate was frozen in 200 ml aliquots. Refractile bodies relatively free from aggregation with cellular debris were visualized under a phase contrast microscope as shown in FIG. 3C as compared with those in FIG. 3B which were from cells disrupted prior to reduction of the ionic strength and show substantial aggregation with cellular debris.

Culture fluid samples (25 ml) at the various volume changes were thawed and sonicated using a tip sonicator for 3×3 min at 50% pulse, 80% maximum energy. Sonicated samples were centrifuged at 33,000×g for 30 minutes. Supernatants and diafiltration permeates were assayed for conductivity and the results are shown in Table 1.

TABLE 1

| CONDUCTIVITIES OF SONICATE SUPERNATANTS AND DIAFILTRATION PERMEATES | | |
|---|---|---|
| DIAFILTRATION VOL CHANGES | PERMEATE CONDUCTIVITY | SONICATE SUP CONDUCTIVITY |
| 2 | 1.97 ms | 3.18 ms |
| 4 | 0.70 ms | 1.41 ms |
| 6 | 0.39 ms | 1.06 ms |
| 8 | 0.30 ms | 1.00 ms |
| 10 | 0.24 ms | 1.00 ms |
| 15 | 0.34 ms | 0.95 ms | ms = millisiemens (siemens is the System Internationale or S.I. unit of electrical conductance having the dimension of 1/ohm.)

Supernatants were also assayed for UV absorbance at 280 and 260 nm and the results are shown in Table 2.

TABLE 2

| UV ABSORBANCE OF SONICATE SUPERNATANTS | | |
|---|---|---|
| VOLUME CHANGES OF SUPERNATANTS DILUTED 100X | $A_{280}$ | $A_{260}$ |
| 2 | 0.73 | 1.37 |
| 4 | 0.73 | 1.38 |
| 6 | 0.73 | 1.37 |
| 8 | 0.74 | 1.39 |
| 10 | 0.74 | 1.39 |
| 15 | 0.75 | 1.40 |

Pellets comprising refractile material were subjectively analyzed for purity. There were two apparent changes occurring with increasing volume changes. First, the size of the sonicated pellet decreased substantially with increasing volume changes. Secondly, the amount of brown pigmented material in the supernatant increased and decreased in the pellet with additional volume changes.

Figure 5:
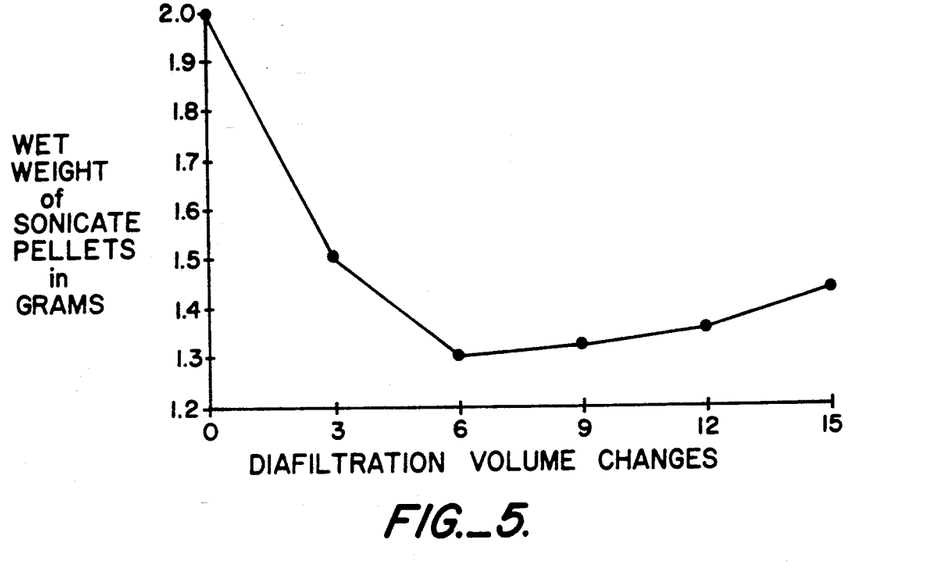
FIG. 5 shows the wet weight of refractile body pellets as a function of diafiltration volume changes.
Figure 6:
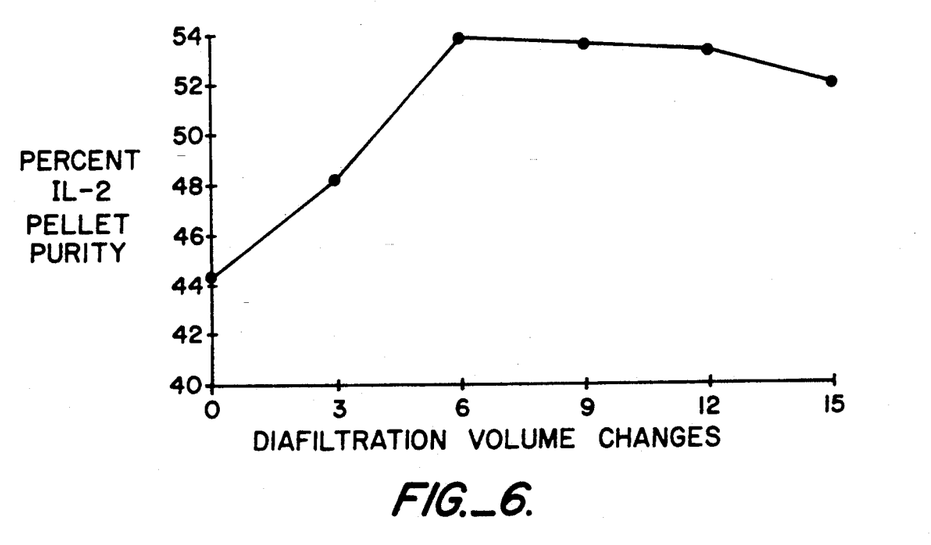
FIG. 6 shows the percent protein which is IL-2 in the refractile body pellet as a function of diafiltration volume changes.

Additional analysis of the pellets comprising refractile material was carried out on harvested cells from a second fermentor growth. Culture conditions, harvest, concentration and diafiltration was carried out as described above except that samples from the culture fluid reservoir were taken at 0, 3, 6, 9, 12 and 15 volume changes and frozen. Each sample was thawed and sonicated using a tip sonicator for 5×3 minutes at 50% pulse, 80% maximum energy. Sonicated samples were centrifuged at 20,000×g for 30 minutes. The appearance of the sonicate pellets were as large brown pigmented pellets at concentrate and initial volume changes, becoming smaller less pigmented pellets with additional volume changes. Wet pellets were weighed and then dissolved in 2% SDS, 100 mM, Tris-HCl, 1 mM EDTA (pH 8.5) and reduced with 50 mM DTT at 40° C. for 10 minutes. The wet weight of sonicate pellets as a function of diafiltration volume changes is shown in FIG. 5. A decrease in pellet mass occurred during the first six diafiltration volume changes. The dissolved pellets were run on RP-HPLC to estimate IL-2 purity in the pellet. The percent purity of IL-2 in the pellet as a function of diafiltration volume changes is shown in FIG. 6. An increase in the purity of IL-2 in the refractile body pellet of about 20% was observed after about six diafiltration volume changes. Approximately six volume changes was sufficient to lower the ionic strength enough for refractile body isolation by a single homogenization operation.

C. Effect of Extended Sonication on Refractile Pellet Composition and Purity.

An aliquot of the final diafiltered cell concentrate prepared as described above was thawed and two 40 ml aliquots taken. One sample (control) was sonicated 5×3 minutes, 50% pulse, 80% maximum energy. The other sample (extended sonicate) was sonicated 15×3 minutes, 50% pulse, 80% maximum energy. The sonicated samples were spun at 20,000×g for 30 minutes and the supernatants decanted. The supernatants were assayed for UV absorbance and the results are shown in Table 3.

TABLE 3

UV ABSORBANCE OF EXTENDED SONICATE AND CONTROL SUPERNATANTS

| SUPERNATANTS 30X DILUTION | $A_{280}$ | $A_{260}$ |
|---|---|---|
| CONTROL | 2.20 | 3.00 |
| EXTENDED SONICATE | 2.23 | 3.17 |

The pellets were qualitatively evaluated and then run on RP-HPLC. The control pellet was a bilayer pellet having a bottom layer of refractile body material and a smaller less dense layer of cell debris on top. The extended sonicate pellet did not have this cell debris layer. Extended sonication appeared to completely "solubilize" all non-refractile cell material. This non-refractile material had little or no UV absorbance as shown by Table 3 indicating that it is neither protein nor nucleic acid. RP-HPLC analysis of the control and extended sonicate pellet showed no difference in the IL-2 purity of the pellets. The additional mass of the control pellet is apparently due to non-proteinaceous materials.

EXAMPLE III

IL-2 Refractile Body Isolation Using Detergents or Surfactants

Cells were grown and concentrated as described in Example II.A. To 250 mls of concentrate cells was added 1-octanol to 0.5% and the mixture was stirred overnight at 4° C. A one square foot hollow fiber Microgon cartridge was employed for diafiltration of the octanol treated cells against 4 volume changes of 1 mM EDTA (pH9.0). Diafiltration was continued with an additional 4 volume changes of 0.5 mM EDTA (pH9.0). 80 mls of diafiltered cell suspension was sonicated 5×2 min. Visualization under a microscope showed predominantly refractile bodies with some whole cells.

To 10 ml aliquots the following additions were made:
(1) none
(2) 50 mM DTT
(3) 50 mM DTT+2% (v/v) nonidet P-40 (NP40)
(4) 50 mM DTT+0.5% (w/v) sodium deoxycholate (DOC)
(5) 50 mM DTT+2% (v/v) NP40+0.5% (w/v) DOC The tubes were incubated 35 min at room temperature. After centrifugation at 8000×g for 10 min at room temperature the supernatants were decanted. Pellets were resuspended and dissolved in an equal volume of 1% SDS and analyzed for absorbance at 260 and 280 nm. The absorbance ratios at 260 nm vs 280 nm are an indication of relative nucleic acid concentration under the various conditions tested. These absorbances for the samples described above were as follows:

| Pellets | $A_{280}$ | $A_{260}$ | $A_{260}/A_{280}$ |
|---|---|---|---|
| (1) | 0.290 | 0.326 | 1.12 |
| (3) | 0.319 | 0.336 | 1.05 |
| (4) | 0.228 | 0.202 | 0.89 |
| (5) | 0.292 | 0.244 | 0.84 |

EXAMPLE IV

Purification of Refractile Bodies Containing Interferon-beta (IFN-$\beta$)

E. coli transformed to produce IFN-$\beta$ is grown as described in commonly owned U.S. Pat. No. 4,737,462. The plasmid designated as clone pSY2501 containing the IFN-$\beta_{ser17}$ mutein is on deposit with the Agricultural Research Culture Collection (NRRL), Fermentation Laboratory, Northern Regional Research Center, Science and Education Administration, U.S. Department of Agriculture, 1815 North University Street, Peoria, Ill. 61604 and assigned accession numbers CMCC No. 1533 and NRRL No. B-15356.

Cells are induced as described in commonly owned U.S. Pat. No. 4,499,188 issued Feb. 12, 1985 and incorporated herein by reference in its entirety and then harvested at a cell density having an $A_{680}$ of about 20–30. Refractile bodies within whole cells are visualized under phase contrast microscope as shown in FIG. 4A. The 10 L culture is concentrated approximately five-fold by cross-flow filtration. The concentrated culture is diafiltered against 6–12 volume changes of 5 mM Tris.HCl, 1 mM EDTA (pH 8.0). The desalted concentrated culture fluid is disrupted by three passes at 7500 psi in a Manton-Gaulin high pressure mechanical cell homogenizer. Refractile bodies at this stage appear substantially free of cellular debris as shown in FIG. 4C in contrast to the aggregated cellular debris containing refractile bodies as shown in FIG. 4B when refractile body isolation is attempted in the absence of a salt removal step such as diafiltration. The insoluble protein fraction containing refractile material is separated from cell debris by continuous centrifugation as described in Example I. The wet pellet is dissolved in 1–2% SDS (w/v) in 0.1M phosphate buffered saline (PBS), pH 7.4.

EXAMPLE V

Refractile Body Isolation Using Membrane Permeability Enhancers

A. Increasing Permeabilization Using Guanidine-HCl and Triton X-100 ®.

Cell cultures are grown and concentrated as described in Examples I, II or IV. Guanidine-HCl is then added to the concentrated culture fluid to a final concentration of 0.5M. Triton X-100 ® is also added to a final concentration of 2% (v/v). Diafiltration is then carried out using 10 volume changes of 5 mM Tris-HCl, 1 mM EDTA (pH 8.0) as the exchange buffer. Culture fluid reservoir samples are taken at 0, 2, 4, 6, 8 and 10 volume changes and after disruption are characterized by microscopic examination for aggregation of cellular debris. The refractile material is separated from cell debris by continuous centrifugation and the wet pellet weight of each sample is determined.

B. Increasing Permeabilization Using Triton X-100 ®

Cell cultures are grown and concentrated as described in Examples I, II or IV. Triton X-100 ® is added to a final concentration of 2% (v/v). Diafiltration is then carried out using 8 volume changes of 5 mM Tris-HCl, 1 mM EDTA (pH 8.0) as the exchange buffer. Culture fluid reservoir samples are taken at 0, 2, 4, 6 and 8 volume changes and after disruption are characterized by microscopic examination for aggregation of cellular debris. The refractile material is separated from cell debris by continuous centrifugation and the wet pellet weight of each sample is determined.

The scope of the invention is not to be construed as limited by the illustrative embodiments set forth herein but is to be determined in accordance with the appended claims.

What is claimed is:

1. A process for recovering refractile material containing a heterologous protein from host microorganisms in a cell culture medium wherein said microorganisms are transformed to produce said heterologous protein, said process comprising the following steps in the following order:
   (a) prior to disrupting said microorganisms, reducing the ionic strength of said culture medium to a level effective in preventing reaggregation of cellular debris with said refractile material after disruption;
   (b) after reducing the ionic strength, disrupting said microorganisms in said culture medium having reduced ionic strength to produce a disruptate;
   (c) separating said refractile material from said cellular debris.

2. A process according to claim 1 wherein step (a) is accomplished by diafiltration.

3. A process according to claim 2 wherein step (a) is accomplished by cross-flow filtration to produce desalted culture fluid.

4. A process according to claim 3 further comprising maintaining said desalted culture fluid at 4° C. for a time between 2 and 20 hours.

5. A process according to claim 4 further comprising repeating step (a) prior to disruption.

6. A process according to claim 1 wherein greater than 99% by weight of the salts are removed from said culture medium in step (a).

7. A process according to claim 6 wherein said salts are removed from said culture medium by diafiltration.

8. A process according to claim 7 wherein said salts are removed from said culture medium by cross-flow filtration.

9. A process according to claim 2 wherein the exchange buffer volume $V_x$ is between five and fifteen times the culture fluid volume $V_c$.

10. A process according to claim 9 wherein $V_x$ is between five and eight times $V_c$.

11. A process according to claim 1 further comprising increasing cell membrane permeability either before or during step (a).

12. A process according to claim 11 wherein said membrane permeability is increased by the addition of a compound or mixture of compounds that results in increased cell membrane permeability.

13. A process according to claim 12 wherein said cell membrane permeability is increased with a compound selected from the group consisting of guanidine-HCl, Triton X-100® and guanidine-HCl plus Triton X-100®.

14. A process according to claim 2 wherein said diafiltration is continued until there is no further decrease in the wet weight of said refractile material separated in step (c).

15. A process according to claim 1 wherein said separation of step (c) is accomplished in the presence of a sugar or mixture of sugars to increase the density or viscosity of said disruptate.

16. A process according to claim 1 further comprising the addition of surfactants to the disrupted cells prior to the centrifugation of step (c).

17. A process according to claim 16 wherein said surfactants are selected from the group consisting of sodium deoxycholate, sodium caprylate, cetyltrimethyl ammonium bromide, nonidet P-40, Triton X-100®, Tween®20, Tween®80 and Brij®.

18. A process according to claim 17 wherein said surfactants are selected from the group consisting of sodium deoxycholate and nonidet P-40.

19. A process according to claim 1 wherein said heterologous protein is selected from the group consisting of M-CSF, IL-2 and IFN-$\beta$.

20. A process according to claim 1 wherein said separation of step (c) results in a monolayer pellet without the addition of a sugar or mixture of sugars to increase the density or viscosity of said disruptate.

* * * * *